United States Patent
Kriech et al.

(10) Patent No.: US 11,091,409 B2
(45) Date of Patent: *Aug. 17, 2021

(54) SAFE AROMATICS

(71) Applicant: Heritage Research Group, Indianapolis, IN (US)

(72) Inventors: Anthony J. Kriech, Indianapolis, IN (US); Julia Austin, Indianapolis, IN (US); Matthew Kriech, Brownsburg, IN (US)

(73) Assignee: Heritage Research Group, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/988,958

(22) Filed: Aug. 10, 2020

(65) Prior Publication Data

US 2021/0017101 A1 Jan. 21, 2021

Related U.S. Application Data

(63) Continuation of application No. 15/916,753, filed on Mar. 9, 2018, now Pat. No. 10,774,016.

(Continued)

(51) Int. Cl.
*C07C 2/70* (2006.01)
*C07C 15/46* (2006.01)
(Continued)

(52) U.S. Cl.
CPC .............. *C07C 2/70* (2013.01); *B01J 27/053* (2013.01); *B01J 31/00* (2013.01); *C07C 15/46* (2013.01); *C01B 17/69* (2013.01); *C10G 2300/1059* (2013.01); *C10G 2300/1096* (2013.01); *C10G 2300/4081* (2013.01); *C10G 2300/80* (2013.01)

(58) Field of Classification Search
CPC ........... C07C 2/70; C07C 2/861; C07C 15/20; C07C 15/38; C07C 15/46; C07C 2527/054; C07C 2527/126; C07C 2531/025; C07C 2603/42; C07C 2603/52; B01J 27/053; B01J 31/00; C10G 2300/1059; C10G 2300/1096; C10G 2300/4081; C10G 2300/80; C10G 29/205
See application file for complete search history.

(56) References Cited

U.S. PATENT DOCUMENTS

| 5,015,797 A | 5/1991 | Lee et al. |
| 5,302,769 A | 4/1994 | Marler et al. |

(Continued)

OTHER PUBLICATIONS

European Patent Application 18764444.8 Extended European Search Report dated Dec. 2, 2020. 8 pages.

(Continued)

*Primary Examiner* — Sharon Pregler
(74) *Attorney, Agent, or Firm* — Woodard, Emhardt, Henry, Reeves & Wagner, LLP

(57) ABSTRACT

A method for reducing the mutagenicity of polycyclic aromatic compounds (PAC's) having one or more bay regions which involves alkylating the PAC's with an alkylating agent in the presence of a catalyst to lower the mutagenicity down to as much as about 0.1. The resulting alkylated polycyclic aromatic compounds retain their physical and chemical properties for safe industrial use including as rubber processing oils, inks, etc.

22 Claims, 1 Drawing Sheet

Polycyclic Aromatic Compounds (PAC's) with known Mutagenic Activity

Related U.S. Application Data

(60) Provisional application No. 62/469,846, filed on Mar. 10, 2017.

(51) Int. Cl.
  *B01J 27/053*  (2006.01)
  *B01J 31/00*  (2006.01)
  *C01B 17/69*  (2006.01)

(56) References Cited

U.S. PATENT DOCUMENTS

| | | |
|---|---|---|
| 5,488,193 A | 1/1996 | Mackerer et al. |
| 5,705,724 A | 1/1998 | Collins et al. |
| 5,900,519 A | 5/1999 | Notte et al. |
| 6,010,617 A | 1/2000 | Mackerer et al. |
| 2015/0148478 A1 | 5/2015 | Trewella et al. |
| 2017/0058212 A1 | 3/2017 | Kumar et al. |
| 2018/0258010 A1* | 9/2018 | Kriech ................. C10G 29/205 |

OTHER PUBLICATIONS

International Search Report and Written Opinion from corresponding PCT application No. PCT/US2018/021712 dated Jun. 29, 2018 (13 pgs).
International Preliminary Report on Patentability and Written Opinion from corresponding PCT application No. PCT/7S2018/021712 dated Sep. 17, 2019.
India Patent Application No. 201917035158 Examination Report dated Mar. 22, 2021. 5 pages.

\* cited by examiner

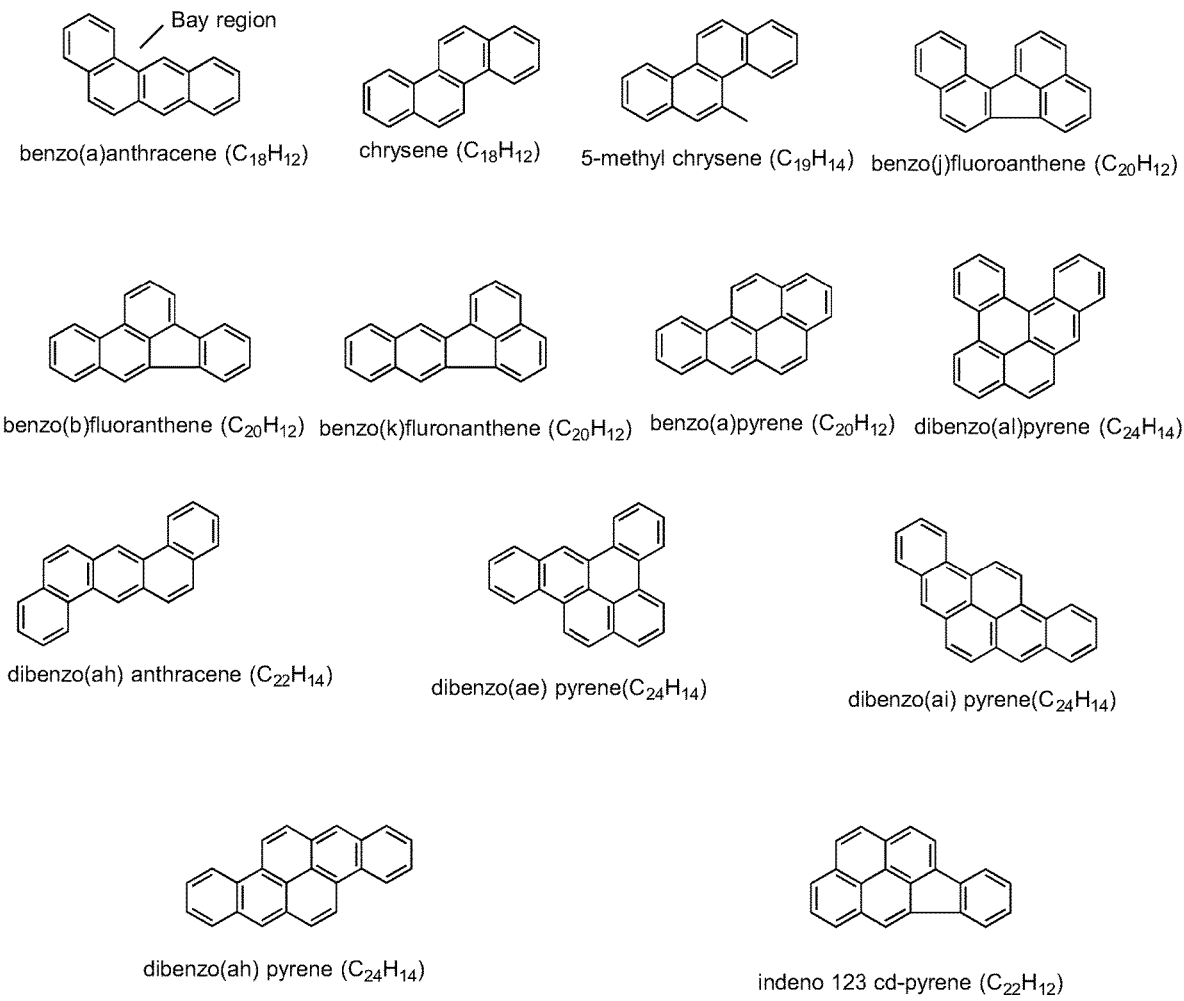
Polycyclic Aromatic Compounds (PAC's) with known Mutagenic Activity

SAFE AROMATICS

RELATED APPLICATION

The present application is a continuation of U.S. application Ser. No. 15/916,753, filed Mar. 9, 2018, which is based upon U.S. Provisional Application Ser. No. 62/469,846, filed Mar. 10, 2017 to which priority is claimed under 35 U.S.C. § 120, and each of which the entire disclosure is hereby expressly incorporated herein by reference.

BACKGROUND

The present invention relates generally to polycyclic aromatic compounds that have one or more bay regions and more specifically to a process for transforming such polycyclic aromatic compounds into safe aromatic oils that have a low mutagenicity (MI) and good physical and chemical properties for safe industrial use including as rubber processing oils and inks.

Heavy Vacuum Gas Oils (HVGO's) that are not processed beyond distillation often contain a measurable proportion of polycyclic aromatic compounds (PACs). A subset of these compounds are classified as carcinogens by Environmental Protection Agency (EPA). A common trait of these carcinogenic PAC's is that they contain bay regions: concave exterior regions formed by three or more phenyl rings that are in a nonlinear arrangement.

FIG. 1 depicts examples of PAC's that have one or more bay regions.

When carcinogenic PAC's enter the body of humans or mammals, the bay regions of aromatic compounds form reactive epoxy-diol intermediates which react with the enzyme system responsible for oxidative metabolism. This reactive intermediate binds with DNA adducts and interrupts normal cell reproduction. A test developed to predict cell mutation is called the Modified Ames test and is used to determine the mutagenicity (MI), i.e. the ability to cause mutation in genetic material.

Historically HVGO's have been relied upon for their ability to provide excellent solvency for the rubber and ink oil industry; however, the use of HVGO's is currently undesirable due to the high carcinogenicity and mutagenicity of the 4-6 member fused aromatics with bay regions.

Many countries require unprocessed HVGO's to include warning labels on Safety Data Sheets to make workers aware of the danger of these compounds due to workplace exposure. The petroleum industry responded to these labeling requirements by further processing of HVGO's to extract PAC's using solvent extraction or converting the PAC's to naphthenic compounds using hydrotreating above 800 psi. These hydrotreatments removed sulfur, nitrogen, and oxygen heterocycling of PAC's. Hydrotreating also saturates the aromatic fused rings with hydrogen making the oils non-carcinogenic and non-mutagenic. These hydrotreated naphthenic oils were deemed safe for worker exposure. However these hydrotreated naphthenic oils lost significant solvency that is required in many of the applications such as rubber processing oils and inks.

The resulting hydrotreated product is a naphthenic oil with low aromaticity (10-25%) and a decrease in performance in the industry. The industry compensates for this decrease in performance by relying on the use of other additives.

In the European Union HVGO's are aggressively extracted with dimethyl sulfoxide (DMSO) to make a product called Treated Distillate Aromatic Extract (TDAE). This process results in an oil with ~25% aromaticity. Several drawbacks to this process are an immediate yield loss of at least 15%, costly solvent usage and/or solvent recovery, extra processing and equipment costs, and the hazardous disposal of highly carcinogenic organic waste.

The alkylation of HVGO compounds with t-butyl chloride/$AlCl_3$ or an olefin such as pentene with a zeolite catalyst can reduce the MI to less that 1 is discussed in U.S. Pat. Nos. 5,488,193 and 6,010,617 to Mackerer et al. This work was performed on a small scale (100 mg PAH) using carbon disulfide ($CS_2$) as a reaction solvent with a suitable alkylation catalyst. No isolation route was investigated. This process was never developed for commercial use.

The alkylation of aromatics proceeds through the formation of the carbonium ion. Reaction of the carbonium with an aromatic forms the arenium ion which then loses a hydrogen as follows:

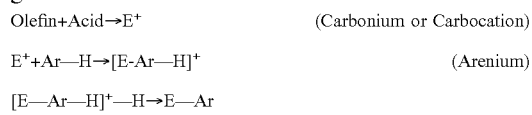

$$\text{Olefin} + \text{Acid} \rightarrow E^+ \quad \text{(Carbonium or Carbocation)}$$

$$E^+ + \text{Ar—H} \rightarrow [\text{E-Ar—H}]^+ \quad \text{(Arenium)}$$

$$[\text{E—Ar—H}]^+ \text{—H} \rightarrow \text{E—Ar}$$

BRIEF SUMMARY

According to various features, characteristics and embodiments of the present invention which will become apparent as the description thereof proceeds, the present invention provides method of reducing the mutagenicity of polycyclic aromatic compounds having one or more bay regions, which method comprises:

obtaining a source of polycyclic aromatic compounds;

contacting the polycyclic aromatic compounds with alkylating agent selected from styrene and hexene in the presence of a catalyst selected from Lewis acids or protonic acids such as $AlCl_3$, sulfuric acid, and methyl sulfonic acid to alkylate the polycyclic aromatic compounds; and recovering the alkylated polycyclic aromatic compounds, wherein the mutagenicity of the alkylated polycyclic aromatic compounds is less than 1.0.

The present invention further provides an alkylated polycyclic aromatic compound which is made by:

obtaining a polycyclic aromatic compound;

contacting the polycyclic aromatic compound with alkylating agent selected from olefins such as styrene and hexene or halogenated aromatic or aliphatics such as t-butyl chloride or chlorobenzene in the presence of a catalyst selected from $AlCl_3$, sulfuric acid, and methyl sulfonic acid to alkylate the polycyclic aromatic compound; and recovering the alkylated polycyclic aromatic compound.

The present invention further provides rubber extender oil that comprises an alkylated polycyclic aromatic compound.

The present invention further provides a rubber article that comprise an alkylated polycyclic aromatic compound.

The present invention also provides an alkylated polycyclic aromatic compound which has been alkylated so as to have a freely rotating aromatic ring attached to a pre-alkylated bay region of the polycyclic aromatic compound.

BRIEF DESCRIPTION OF THE DRAWING

FIG. 1 depicts examples of PAC's that have one or more bay regions.

DETAILED DESCRIPTION OF THE DRAWINGS AND THE PRESENTLY PREFERRED EMBODIMENTS

The present invention relates generally to PAC's that have one or more bay regions and more specifically to a process for transforming such polycyclic aromatic compounds into safe aromatic oils that have a low mutagenicity (MI) and good physical and chemical properties for safe industrial use including as rubber processing oils and inks.

The PAC's of the present invention have mutagenicity values as low as about 0.1 which provides a degree of safety greatly needed in the art.

During the course of the present invention, Heavy Vacuum Gas Oil, several HVGC distillation cuts from HVGO, Light Cycle Oil, and Cat Cracker Slurry, and several naphthenic oils with low aromatics were tested as the feedstock oils to be alkylated.

Catalysts tested for the alkylation included US-Y zeolite, Amberlite 15 and 36, $AlCl_3$, sulfuric acid, methane and p-toluene sulfonic acids although other Lewis acids, protonic acids and superacids can be used to alkylate.

Alkylating reagents tested included butene, hexene, naphthalene, styrene, t-BuCl, and benzyl chloride. It was determined that other olefins and halogenated aromatics can be used in place of these alkylating reagents depending on the catalyst system used.

As the result of the alkylation testing styrene is the chosen olefin for alkylation. In this regard it was discovered that styrene is better at blocking the bay region than t-butyl chloride or hexene. It is believed that the reason styrene performed better was probably due to the freely rotating aromatic ring of the ethylbeneze side chain formed from the alkylation. Since the resulting oil retains its aromaticity (46%) it was anticipated that the product would have the desired high solvency with low mutagenicity.

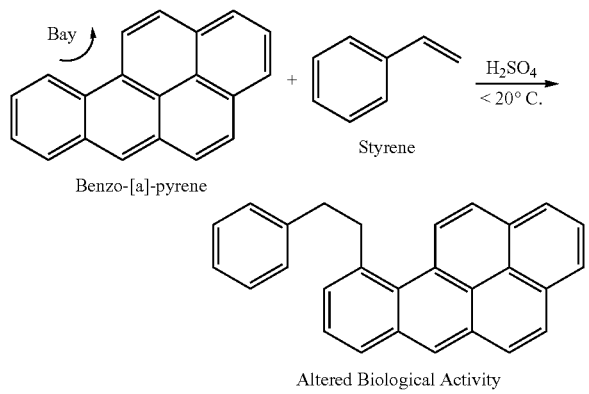

Examples

Features and characteristics of the present invention will be exemplified by the following examples which are provided as non-limiting examples only Examples of Alkylation:

In the following examples un-hydrotreated HVGO having a Σ4-6 ring PAC content of 170 ppm and a mutagenicity index (MI) of 7.5 was subjected to alkylation as described. The target MI was <1.

HVGO with t-butyl chloride and $AlCl_3$

In this example 100 grams of the HVGO was alkylated with 102 grams (1.01 moles) of t-butyl chloride in the presence of 22 grams $AlCl_3$ in hexane while being refluxed. After alkylation the catalyst was quenched with water and the product was distilled to remove unreacted t-butyl chloride. After alkylation the Σ4-6 ring PAC's in the product were reduced to 0 ppm and MI was 0.89.

In this example 100 grams of HVGO was alkylated with 66 grams (0.72 moles) of t-butyl chloride in the presence of 7 grams of $AlCl_3$ in hexane while being refluxed. After alkylation the catalyst was quenched with water and the product was distilled to remove unreacted t-butyl chloride. After alkylation the Σ4-6 ring PAC's in the product were reduced to 11.9 ppm and the MI was 1.30.

HVGO with Styrene and $H_2SO_4$

In this example 100 grams of HVGO was alkylated with 75 grams (0.72 moles) of styrene in the presence of 20 grams of sulfuric acid at a temperature of less than 20° C. After alkylation the catalyst was quenched using either an aqueous solution of NaOH or $NH_4OH$ and the product was distilled to remove unreacted styrene and light end materials. After alkylation the Σ4-6 ring PAC's in the product were reduced to 12.7 ppm and the MI was 0.14.

In this example 100 grams of HGO was alkylated with 45 grams (0.43 moles) of styrene in the presence of 30 mL methane sulfonic acid at a temperature of less than 20° C. After alkylation the catalyst was phase separated and the product is distilled to remove unreacted styrene and light end materials. After alkylation the Σ4-6 ring PAC's in the product were reduced to 13.1 ppm and the MI was 0.60

In this example 100 grams of HVGO was distilled to remove 25% of the light ends and then alkylated with 30 grams (0.29 moles) styrene in 20 grams of sulfuric acid at a temperature of less than 20° C. After alkylation the catalyst was quenched using either an aqueous solution of NaOH or $NH_4OH$ and the product was is distilled to remove unreacted styrene and light end materials. After alkylation the Σ4-6 ring PAC's in the product were reduced to 22.8 ppm and the MI was 0.77. The flash point for this product was 410° F.

Mutagenicity Based on Blocking Groups:

Based on the above examples styrene was determine to be more effective at blocking the bay regions and reducing the MI (see Table 1). Using t-BuCl, the MI at 0 ppm of Σ4-6 ring PAC's is 0.89. The presence of as little as 11.9 ppm of these species increase the MI above the target to 1.3 (Run numbers 2 and 1, respectively)

TABLE 1

Comparison of MI for t-BuCl and Styrene Alkylations

| | Run Number | | | | |
|---|---|---|---|---|---|
| | 1 | 2 | 3 | 4 | 51 |
| Oil source | UHVGO | UHVGO | UHVGO | UHVGO | 25% distilled UHVGO |
| MI | 1.3 | 0.89 | 0.14 | 0.6 | 0.77 |
| Sum of 4-6 PAC's | 11.90 | 0.00 | 12.70 | 13.13 | 22.84 |
| Alkylating reagent | t-BuCl | t-BuCl | Styrene | Styrene | Styrene |
| Moles | 1.01 | 0.72 | 0.72 | 0.43 | 0.29 |
| Catalyst | AlCl3 | AlCl3 | H2SO4 | MSA | H2SO4 |

Using the same moles of styrene (0.72 moles) used to achieve 0 ppm with t-BuCl reduces the Σ4-6 ring PAC's to 12.7 ppm; however, the MI is reduced to 0.14 compared to 0.89 (Run 3 vs. Run 2). This indicates on a mole-to-mole basis, the styrene is more efficient at blocking the bay regions.

Reducing the moles of styrene by 60% to 0.43 moles still results in a passing MI. Distilling 25% of the light end of the oil to increase flash point of the product and reducing the moles of styrene further to 0.29 results in a passing MI of 0.77.

Other Tested Systems:

From the results of the examples above it was determined that the method for alkylation shows potential for other carcinogenic oil streams including light cycle oil, reclamite B, and cat cracker slurry. These oil streams alkylated as summarized in Table 2 below Canadian market. In the EU, these oils are aggressively solvent extracted to product a passing oil, TDAE. The treatment of this oil results in a loss of the aromaticity and yield loss. In addition there is a high cost associated with disposal of the by-product solvent stream that is high in PAC's.

During the course of the present invention it was discovered that HVGO that has 25% of the lights removed and is alkylated according to the present invention results in an aromatic oil that is not only non-carcinogenic, but also has physical and chemical properties similar to that of the Sundex 790 (See Table 3).

TABLE 3

Physical and Chemical Properties of Alkylated HVGO and other Rubber Extender Oils

| Sample | Sundex | DAE[3] | TDAE[3] | Oil Treated by Invention | Method |
|---|---|---|---|---|---|
| Σ4-6 PAC's - ppm | 138.4 | — | <10 | 22.84 | GC-TOF |
| Mutagenicity Index | Fail | Fail | Pass | 0.77 | AMES test for MI |
| API Gravity (60° F.) | 13.8 | — | — | 14.1 | D4052 |
| Specific Gravity g/cm-3 | 0.9738 | — | — | 0.9722 | D4052 |
| Pound/Gallon | 8.11 | — | — | 8.10 | Calculation |
| Flash Point F | 473 | — | — | 410 | COC |
| Sulfur | 0.93 | 1.2 | 0.8 | 2.2 | D4294/D2622 |
| Viscosity (40° C.) cSt | 432 | 1240 | 410 | 410.5 | D445 |
| Viscosity (100° C.) cSt | 16.1 | 28 | 20 | 13.5 | D445 |
| VGC | 0.938 | — | — | 0.937 | Calculation |
| Refractive Index | 1.0604 | — | — | 1.0529 | D1747 |
| $C_{aromatic}$ | 41 | 35 | 30 | 46 | Calculation from |
| $C_{paraffinic}$ | 42 | 35 | 45 | 24 | RI and VCG |
| $C_{naphthenic}$ | 17 | 40 | 25 | 30 | |

[3]Petroleum-Based Safe Process Oils in NR and NR/SBR Blends: Effects of Oil Types and Contents on the Properties on Carbon Black Filled Compounds - J. W. M Noodermeer, University of Twente, Netherlands

TABLE 2

Alternative Oils and Alkylating Reagents

| Oil tested | HVGO | Light Cycle Oil | Reclamite B | Cat Cracker Slurry |
|---|---|---|---|---|
| Alkylating reagent | Hexene | Styrene | Styrene | Styrene |
| Catalyst | $H_2SO_4$ | $H_2SO_4$ | $H_2SO_4$ | $H_2SO_4$ |
| ppm Starting Σ4-6 ring PAC's | 170 | 253.7 | 222.8 | 10872 |
| ppm Product Σ4-6 ring PAC's | 32.5 | 0 | 71.3 | 4708 |
| % Reduction of Σ4-6 ring PAC's | 80.8% | 100% | 67.8% | 56.7% |

From the test results presented in Table 2 it can be seen that alkylation shows significant reductions in PAC's for all the different oils tested as well as reduction using hexene with HVGO.

Comparison of Analytical of Alkylated HVGO to Other Rubber Extender Oils

In addition to lowering MI (and Σ4-6 ring PAC's) the physical and chemical properties of the alkylated oils were tested during the course of the present invention to determine if the functionality of the alkylation of the oils where adversely effected.

Currently, Sundex 790N aromatic oil is used in the US market to compatibilize rubber for processing tires and other rubber products. Sundex oil is a carcinogen due to the high level of PAC's. Sundex oil will eventually be phased out of the U.S. market as it was in the EU and likely will be in the As seen from the data in Table 3 alkylation of HVGO containing PAC's using styrene under acid conditions has higher aromatic content than either Sundex 790N or TDAE with a mutagenicity index comparable to TDAE and much lower than Sundex. In addition, the viscosity and specific gravity are comparable to the two oils. Flash point of the alkylated HVGO is high enough to be used in the vulcanization process.

The work conducted during the course of the present invention demonstrates that safe aromatic oils with low MI and good physical and chemical properties can be prepared by alkylation. Such safe aromatic oils can be used to compatibilize rubber for processing tires and other rubber products and in other processes in which PCA's have been used.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and set forth in the attached claims.

The invention claimed is:

1. A method of reducing the mutagenicity of polycyclic aromatic compounds having one or more bay regions, which method comprises:
   obtaining a composition comprising one or more polycyclic aromatic compounds;

contacting the composition comprising polycyclic aromatic compounds with alkylating agent selected from styrene and hexene in the presence of a catalyst selected from Lewis acids and protonic acids to alkylate the polycyclic aromatic compounds to provide one or more polycyclic aromatic compounds that are alkylated at a position blocking the at least one bay region; and recovering the alkylated polycyclic aromatic compounds, wherein the mutagenicity of the alkylated polycyclic aromatic compounds is less than 1.0.

2. The method of reducing the mutagenicity of polycyclic aromatic compounds according to claim 1, wherein the composition comprising one or more polycyclic aromatic compounds is selected from heavy vacuum gas oils, light cycle oil, reclamite B, and a cat cracker slurry.

3. The method of reducing the mutagenicity of polycyclic aromatic compounds according to claim 2, wherein the composition comprising one or more polycyclic aromatic compounds comprise heavy vacuum gas oils.

4. The method of reducing the mutagenicity of polycyclic aromatic compounds according to claim 3, wherein the alkylating agent is styrene and the catalyst is a protonic acid.

5. The method of reducing the mutagenicity of polycyclic aromatic compounds according to claim 1, wherein the mutagenicity of the alkylated polycyclic aromatic compounds is 0.8 or less.

6. The method of reducing the mutagenicity of polycyclic aromatic compounds according to claim 5, wherein the mutagenicity of the alkylated polycyclic aromatic compounds is 0.5 or less.

7. The method of reducing the mutagenicity of polycyclic aromatic compounds according to claim 6, wherein the mutagenicity of the alkylated polycyclic aromatic compounds is 0.3 or less.

8. The method of reducing the mutagenicity of polycyclic aromatic compounds according to claim 1, wherein the composition comprising one or more polycyclic aromatic compounds is distilled prior to contacting the polycyclic aromatic compounds with the alkylating agent in the presence of the catalyst.

9. An alkylated polycyclic aromatic compound which is made by:
obtaining a composition comprising one or more polycyclic aromatic compound comprising at least one bay region;
contacting the polycyclic aromatic compound comprising at least one bay region with alkylating agent selected from styrene and hexene in the presence of a catalyst selected from Lewis acids or protonic acids to alkylate the polycyclic aromatic compound at a position blocking the at least one bay region; and
recovering the alkylated polycyclic aromatic compound.

10. An alkylated polycyclic aromatic compound according to claim 9, wherein the composition comprising one or more polycyclic aromatic compounds is selected from of heavy vacuum gas oils, light cycle oil, reclamite B, and a cat cracker slurry.

11. An alkylated polycyclic aromatic compound according to claim 10, wherein the composition comprising one or more polycyclic aromatic compounds comprise heavy vacuum gas oils.

12. An alkylated polycyclic aromatic compound according to claim 9, wherein the alkylating agent is styrene and the catalyst is sulfuric acid.

13. An alkylated polycyclic aromatic compound according to claim 9, wherein the mutagenicity of the alkylated polycyclic aromatic compounds is 0.8 or less.

14. An alkylated polycyclic aromatic compound according to claim 13, wherein the mutagenicity of the alkylated polycyclic aromatic compounds is 0.5 or less.

15. An alkylated polycyclic aromatic compound according to claim 14, wherein the mutagenicity of the alkylated polycyclic aromatic compounds is 0.3 or less.

16. An alkylated polycyclic aromatic compound according to claim 9, wherein the composition comprising one or more polycyclic aromatic compounds is distilled prior to contacting the polycyclic aromatic compounds with the alkylating agent in the presence of the catalyst.

17. An alkylated polycyclic aromatic compound according to claim 9, wherein the alkylated polycyclic aromatic compound comprises rubber extender oil.

18. A rubber article that comprise an alkylated polycyclic aromatic compound according to claim 9.

19. An alkylated polycyclic aromatic compound which has been alkylated so as to have a freely rotating aromatic ring attached to a pre-alkylated bay region of the polycyclic aromatic compound.

20. The method of reducing the mutagenicity of polycyclic aromatic compounds according to claim 1, wherein the catalyst selected from $AlCl_3$, sulfuric acid, and methyl sulfonic acid.

21. The method of reducing the mutagenicity of polycyclic aromatic compounds according to claim 4, wherein the catalyst selected from sulfuric acid, and methyl sulfonic acid.

22. The method of reducing the mutagenicity of polycyclic aromatic compounds according to claim 9, wherein the catalyst selected from $AlCl_3$, sulfuric acid, and methyl sulfonic acid.

* * * * *